United States Patent [19]

Halm et al.

[11] Patent Number: 4,962,219

[45] Date of Patent: Oct. 9, 1990

[54] ALKYLATION OF HALODISILANES

[75] Inventors: Roland L. Halm, Madison; Kirk M. Chadwick, Hanover, both of Ind.; Brian R. Keyes, Salt Lake City, Utah

[73] Assignee: Dow Corning Corporation, Midland, Mich.

[21] Appl. No.: 439,073

[22] Filed: Nov. 17, 1989

Related U.S. Application Data

[63] Continuation-in-part of Ser. No. 258,949, Oct. 17, 1988, abandoned.

[51] Int. Cl.$^5$ ............................................. C07F 7/08
[52] U.S. Cl. .................................................... 556/468
[58] Field of Search ........................................ 556/468

[56] References Cited

U.S. PATENT DOCUMENTS

| | | | |
|---|---|---|---|
| 2,403,370 | 7/1946 | Hurd | 260/607 |
| 2,413,582 | 12/1946 | Rust et al. | 260/607 |
| 2,474,087 | 6/1949 | Barry et al. | 556/468 |
| 2,598,434 | 5/1952 | Nobler | 556/468 |
| 2,636,895 | 4/1953 | Walton | 556/468 |
| 2,762,824 | 9/1956 | Brown | 260/448.2 |
| 2,857,414 | 10/1958 | Schmidt | 260/448.2 |
| 2,945,874 | 7/1960 | Jenkner | 260/448.2 |
| 3,065,253 | 11/1963 | Merritt | 260/448.3 |
| 3,772,347 | 11/1973 | Atwell et al. | 556/468 |
| 4,059,607 | 11/1977 | Rudy et al. | 556/468 |
| 4,155,927 | 5/1979 | Straussberger et al. | 556/468 |
| 4,158,010 | 6/1979 | Graf et al. | 260/448.2 |
| 4,289,890 | 9/1981 | Gordon | 556/430 |
| 4,309,556 | 1/1982 | Allain et al. | 556/430 |
| 4,400,528 | 8/1983 | Artes | 556/430 |
| 4,578,495 | 3/1986 | Soula et al. | 556/468 |

FOREIGN PATENT DOCUMENTS 689436 3/1953 United Kingdom ............... 556/478

OTHER PUBLICATIONS

Hurd, J. Amer. chem. soc., vol. 67 (1945), pp. 1545–1548.

Kumada et al., J. Org. Chem., vol. 21 (1956), pp. 1264–1268.

*Primary Examiner*—Paul F. Shaver
*Attorney, Agent, or Firm*—James E. Bittell

[57] ABSTRACT

A process for the preparation of more highly alkylated silanes and disilanes. The process comprises (A) contacting a halodisilane, with an alkyl halide in the presence of a metal, such as aluminum, which serves as a halogen acceptor, (B) reacting the halodisilane with the alkyl halide in the presence of the metal at a temperature greater than about 150° C. to form the more highly alkylated silanes and disilanes and a metal halide; and (C) isolating and separating the more highly alkylated silanes and disilanes.

30 Claims, No Drawings

ALKYLATION OF HALODISILANES

This is a continuation-in-part of copending application Ser. No. 07/258,949 filed on 10/17/88, now abandoned.

BACKGROUND OF THE INVENTION

This invention relates to the addition of alkyl groups to halodisilanes to produce more highly alkylated organosilanes and organodisilanes.

In the silicones industry organosiloxanes are prepared from the hydrolysis of organohalosilanes. The predominant starting organohalosilanes are the diorganodihalosilanes which produce diorganopolysiloxanes materials utilized in fluids, high-molecular weight linear polymers used in silicone elastomers, and the like. Organohalosilanes are primarily produced by the direct reaction of silicon and organic halides, as first disclosed by Rochow and his co-workers in the 1940's. The direct reaction can be controlled so that the predominant component is the diorganodihalosilane. However, other products of lower commercial value are also produced. These other products include tetrahalosilanes, organotrihalosilanes, helodisilanes, organohalodisilanes, and similar more highly halogenated species. It would be advantageous if such highly halogenated species could be efficiently converted to the more useful diorganodihalosilanes. Additionally, the demand for silanes of higher organic content such as triorganohalosilanes is often greater than the supply from the direct reaction. Further, more highly alkylated disilanes are chemical intermediates of interest.

As an early example of the preparation of organosilicon compounds using metallic reagents, Kipping and Dilthey both demonstrated the alkylation of tetrachlorosilane via reaction with an organ0 magnesium halide, the well-known Grignard process.

Hurd, *J. Am. Chem. Soc.* (1945), vol. 67, pp. 1545–1548, and Hurd, U.S. Pat. No. 2,403,370, issued July 2, 1946, disclose the alkylation of tetrachlorosilane and various methylchlorosilanes by passing the vapors of these chlorosilanes together with an alkyl halide over finely divided aluminum, zinc, or other reactive metal at elevated temperatures of 300° to 500° C. Hurd discloses that a reaction occurs under these conditions in which chlorine groups on the chlorosilane are replaced by alkyl groups.

Artes et al., U.S. Pat. No. 4,400,528, issued Aug. 23, 1983, discloses a process for methylating silicon compounds containing halogen and at least 2 silicon atoms with tetramethylsilane in the presence of at least one organoaluminum compound in the presence of a hydrogen-containing silane. The process disclosed by Artes et al. is a liquid phase reaction.

SUMMARY OF THE INVENTION

The objective of the instant invention is providing a process for the preparation of more highly alkylated organosilanes and organodisilanes from the reaction of halodisilanes with an alkyl halide in the presence of a halogen-accepting metal.

It has been found that halodisilanes can be alkylated to more highly alkylated organodisilanes. Further, it has been found that a significant portion of the halodisilanes are converted to usable organosilanes. It was then found that the alkylation of halodisilanes can be significantly improved by the addition of a catalyst.

DESCRIPTION OF THE INVENTION

The instant invention provides for a process for the alkylation of halodisilanes to produce more highly alkylated silicon compounds. What is described, therefore, is a process for preparing more highly alkylated silicon compounds having the formula,

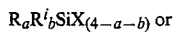
$R_a R^i_b SiX_{(4-a-b)}$ or

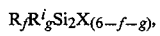
$R_f R^i_g Si_2 X_{(6-f-g)}$, wherein each R is independently selected from a group consisting of methyl, ethyl, and n-propyl; each $R^i$ is independently selected from a group consisting of hydrogen atoms, alkyl, substituted alkyl, alkenyl, aryl, and alkaryl groups; a has a value of 0, 1, 2, 3, or 4, b has a value of 0, 1, 2, 3, or 4, and the sum of a+b is 4 or less; f has a value of 0, 1, 2, 3, 4, 5, or 6; g has a value of 0, 1, 2, 3, 4, 5, or 6, and the sum of f+g is 6 or less; the sum of a+f is greater than zero and less than 11; and X is an independently selected halogen atom,
said process comprising:

(A) contacting a halodisilane, having the formula,

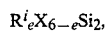
$R^i_e X_{6-e} Si_2$, or a mixture thereof, wherein $R^i$ and X are defined above; and e has a value of 0, 1, 2, 3, 4, or 5, with an alkyl halide, having the formula,

RX, wherein R and X are defined above, in the presence of a metal which serves as a halogen acceptor;

(B) reacting the halodisilane with the alkyl halide in the presence of the metal at a temperature greater than about 150° C. to form the more highly alkylated silicon compounds and a halide of the metal; and (C) isolating and separating the more highly alkylated silicon compounds.

The process for alkylating halodisilanes can further comprise reacting the halodisilane with the alkyl halide in the presence of a metal which serves as a halogen acceptor in the presence of a sufficient quantity of a catalyst effective in improving exchange of said R groups from the alkyl halide with said halogen atoms X of said halodisilane to yield said more highly alkylated silicon compounds.

The metal which serves as a halogen acceptor can be selected from a group consisting of aluminum and zinc. The preferred metal is aluminum. The metal can be in the physical form, for example, of powders, wire, flake, granules, and chunks. It is preferred that the form of the metal expose as much surface area as possible to facilitate contact with the halide of silicon and the alkyl halide.

For the purposes of the instant invention, "a catalyst effective in improving exchange of said R groups from the alkyl halide with said halogen atoms X of said halide of silicon to yield said more highly alkylated silanes" is a material that provides the benefits, individually or in combination, of (1) shortened induction time to reach steady-state alkylation conditions; (2) increased conversion of the reactant halides of silicon and alkyl halide; and (3) increased overall incorporation of alkyl groups generated from the reacted alkyl halides into the reacted halides of silicon. As an example, as shown in the examples infra, in the reaction of methyl chloride with a halodisilane in the presence of aluminum about 50 mole percent of the methyl groups available for exchange are incorporated in the final methyl-containing silicon compounds. Addition of a catalyst, such as tin metal or a tin compound at levels of greater than about 3000 parts per million, based upon the weight of the aluminum, raises methyl incorporation to as high as 100 mole percent at the same conditions of temperature and contact time.

It is known in the art that certain compounds attack aluminum. Examples of these compounds are hydrogen chloride, magnesium chloride, zinc chloride, phosphorus, and ferric chloride. It is theorized that catalysts that are effective at increasing alkyl/halogen exchange in the above reaction are those materials that improve contact of the vapors of the reactant alkyl halide and halide of silicon with the halogen-accepting metal by facilitating increased penetration or disruption of a metal oxide film or layer on the surface of the halogen-accepting metal. However, the instant invention is not limited by this theory.

The catalyst can include, for example, tin metal and tin compounds, antimony and antimony compounds, aluminum bromide, boron, phosphorous, and metal phosphorous alloys or metal phosphides, palladium, iodine, iron chloride, hydrogen halides, copper and copper compounds, and mixtures thereof. In considering aluminum as the halogen-accepting metal, the catalyst can further include mercury and mercury compounds, zinc and zinc compounds, and mixtures thereof. It is understood that the catalyst is not limited to these materials or compounds used as examples. Any material or compound Which functions in an equivalent manner to improve contact of the vapors of the reactant alkyl halide and halide of silicon with the halogen-accepting metal by facilitating increased penetration or disruption of a metal oxide film or layer on the surface of the halogen-accepting metal is intended to be encompassed by the instant invention. The preferred catalysts are tin and tin compounds. The most preferred catalyst is tin metal.

"A sufficient quantity of catalyst" varies with the particular catalyst. However, most catalysts are effective at concentrations of greater than about 3000 parts per million (ppm) by weight, based upon the weight of the halogen-accepting metal. The inventors project that amounts lower than 3000 ppm are effective as a catalyst. Thus it is projected that levels of catalysts of 100 ppm or greater are effective in increasing alkyl/halogen exchange. However, these lower amounts of catalyst are susceptible to inactivation and poisoning by impurities within the process. The inventors project that higher levels of catalysts can be utilized, but no additional benefit is anticipated.

When copper or copper compounds are used as a catalyst, a preferred concentration is about 3000 to 60,000 ppm copper. Higher concentrations of copper can be employed, but no advantage is perceived. Lower concentrations of copper may also work, but with reduced efficiency of alkyl/halogen exchange. The catalytic activity of copper and copper compounds is improved by the presence of tin, tin compounds, zinc, zinc compounds, and mixtures thereof. A preferred concentration is about 50 to 3000 ppm zinc and/or tin.

The catalyst may be combined with the metal which serves as a halogen acceptor as a heterogeneous mixture of solids. The catalyst may also be combined as an alloy with the halogen accepting metal. The catalyst can be in the physical form, for example, of powders, granules, flakes, chips, or pellets.

The more highly alkylated silicon compounds can be, for example, tetramethylsilane, tetraethylsilane, dimethyldiethylsilane, trimethylchlorosilane, triethylfluorosilane, dimethyldichlorosilane, diethyldibromosilane, methyltrichlorosilane, ethyldimethylchlorosilane, ethylmethyldichlorosilane, dimethylvinylchlorosilane, triethylallylsilane, trifluoropropylmethyldichlorosilane, trifluoropropyldimethylchlorosilane, methylphenyldichlorosilane, and diphenylmethylchlorosilane, hexamethyldisilane, hexaethyldisilane, 1,1,2-trimethyl-1,2,2-trichlorodisilane, 1,1,2,2-tetraethy-1-methyl-2-bromodisilane, or 1-ethyl-1,2,2-trimethyl-1,2-dichlorodisilane.

The halodisilanes which will be enriched in alkyl groups are selected from halodisilanes, and organohalodisilanes. These materials are represented by the formula,

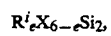
$R^i_e X_{6-e} Si_2$, wherein $R^i$ and X are defined above, and wherein e has a value of 0, 1, 2, 3, 4, or 5. Each $R^i$ can be a hydrogen atom; an alkyl group, for example, a hydrocarbon group containing 1 to 10 carbon atoms; a substituted alkyl group, for example, chloromethyl or trifluoropropyl; an alkenyl group, for example, vinyl, allyl, or hexenyl; or an aryl or alkaryl group, for example, phenyl, tolyl, or benzyl.

The halodisilane can be, for example, hexafluorodisilane, hexabromodisilane, or hexachlorodisilane. The organohalodisilane can be, for example, 1,2-dimethyl-1,1,2,2-tetrachlorodisilane, 1,1,2,2-tetraethyl-1,2-dibromodisilane, or 1,2-dimethyl-1,1,2,2-tetrachlorodisilane. It is understood that the halodisilanes can be a mixture of halodisilanes. It is further understood, that the halodisilanes can be combined in a mixture of other compounds such as silalkylenes and other silicon-containing and organic compounds. An example of such a mixture is the high-boiling residue from crude methylchlorosilane prepared by the direct reaction of methyl chloride with silicon.

The alkyl halide can be, for example, methyl fluoride, methyl bromide, methyl chloride, ethyl fluoride, ethyl bromide, ethyl chloride, and n-propyl bromide. Methyl chloride and ethyl chloride are preferred alkyl halides.

The molar ratio of the halodisilanes and the alkyl halide fed to the reactor is not critical. The molar ratio can vary depending upon the starting reactants, the desired product, and the reaction conditions. Examples of molar ratios are utilized are illustrated in the examples, infra.

Contacting the halodisilane and the alkyl halide in the presence of a metal which serves as a halogen acceptor can be effected by known means for gas-solid contact. Such contact can be effected by vaporizing the halodisilane and the alkyl halide and feeding these vapors combined or separately to a vessel containing the solid metal and catalyst. The solids can be configured in such contact arrangements as a packed bed, a stirred bed, a vibrating bed, or a fluidized bed.

To facilitate reaction of the halodisilane, the alkyl halide, and the metal, a vessel should have provisions to control the temperature of the contact zone. For continuous operation, the vessel should include provisions to replenish the halogen-accepting metal as it is converted to a metal halide.

The temperature in the contact zone to effect reaction should be greater than about 150° C. Preferably the temperature in the contact zone should be in a range from about 150° to 400° C. More preferably, the temperature should be in a range from about 150° to 250° C. Little reaction is projected to take place at temperatures less than 150° C. Temperatures in excess of 400° C. are not desirable since the rate of cleavage of organic groups from silicon can be significant at these higher temperatures. Additionally, the rate of decomposition of alkyl chlorides at higher temperatures is also increased.

Residence time of the gaseous halodisilane and the alkyl halide in contact with the halogen-accepting metal and the catalyst should be greater than about 0.5 seconds. It is preferred that residence time be in a range from about 1 to 15 seconds.

Isolating and separating the more highly alkylated silicon compounds can comprise (D) separating metal halide from gaseous more highly alkylated silicon compounds, unreacted halodisilane, and unreacted alkyl halide; and (E) isolating the more highly alkylated silicon compounds from the unreacted halodisilanes and the alkyl halide.

The metal halide can be a vapor at the conditions of the reaction. Separating the metal halide from the more highly alkylated silicon compounds and remaining reactants can be effected by such known methods as cooling the vapor stream exiting the contact vessel to a temperature low enough to allow recovery of the metal halide as a solid while passing the product silanes and disilanes and remaining reactants through as a vapor. The metal halides can also remain in the reactor. The vapor stream of gaseous product, more highly alkylated silicon compounds, disilanes, and remaining reactants can be condensed to a liquid crude product. The more highly alkylated silicon compounds can be isolated in high purity from the remaining reactants by such known methods as distillation.

The aluminum powder was Alcan 44, atomized aluminum powder, purchased from Alcan-Toyo American, Joliet, Ill.

Methyl chloride (MeCl) was fed as a gas from a compressed gas cylinder. Methyl chloride flow was controlled by a mass flow meter. The halodisilane feed, dimethyltetrachlorodisilane (DMTCDS), began as a liquid feed from a positive displacement pump. The MeCl and DMTCDS feeds were passed through approximately 4 feet of coiled stainless steel tubing in the heated fluidized sand bath.

DMTCDS feed rate was 11.9 g/hr. MeCl feed rate was 8.7 g/hr. Feeds were continued for 396 minutes. The mole ratio of MeCl/DMTCDS was 3.3/1. At the reactor temperature, the residence time for the feed bases 13.1 seconds.

The vapors exiting the reactor passed through a heated trap, temperature controlled at approximately 155° C., to remove $AlCl_3$ from the vapor stream as a solid. The remaining vapors were passed to a cold trap to recover the unreacted MeCl and the resultant methylchlorosilane mixture. The liquid crude product was then analyzed by gas chromatography (GC).

Table 1 is a summary of the results of this run. The results of crude product GC analysis is represented on a MeCl/DMTCDS-free basis in area percent. The components were tetramethylsilane ($Me_4$), trimethylchlorosilane ($Me_3$), dimethyldichlorosilane ($Me_2$), trimethyltrichlorodisilane ($Me_3Si_2$), tetramethyldichlorodisilane ($Me_4Si_2$), pentamethylchlorodisilane ($Me_5Si_2$), and hexamethyldisilane ($Me_6Si_2$), designated as "$Me_4$", "$Me_3$", "$Me_2$", "Disilanes": "$Me_3$", "$Me_4$", "$Me_5$", and "$Me_6$", respectively, in Table 1. Based upon product recovery, feed composition and product analyses, conversion of starting DMTCDS, conversion of MeCl, and percent of MeCl converted that was incorporated in the more highly methylated product chlorosilanes were calculated. These results are reported in Table 1, as "% SiCl Conv", "% MeCl Conv", and "% Me Eff", respectively.

TABLE 1

| | | Disilanes | | | | | % SiCl | % MeCl | |
|---|---|---|---|---|---|---|---|---|---|
| $Me_4$ | $Me_3$ | $Me_2$ | $Me_3$ | $Me_4$ | $Me_5$ | $Me_6$ | Conv | Conv | % Me Eff |
| 0.8 | 59.8 | 25.0 | 1.0 | 5.0 | 1.5 | 0.3 | 70.1 | 51.4 | 51.5 |

So that those skilled in the art may better understand and appreciate the instant invention, the following examples are presented. These examples are presented to be illustrative and are not to be construed as limiting the claims as delineated herein.

EXAMPLE 1

An apparatus was assembled for the alkylation of halodisilanes via the reaction of a halodisilane with an alkyl halide in the presence of aluminum metal.

A carbon steel cylinder approximately 1 inch in diameter by about 10 inches in length was utilized as a reaction tube. The reaction tube was charged with 89.1 g of aluminum. The volume of the reactor filled with aluminum was about 72.4 cc. Reaction temperature was about 250° C. The cylinder was placed in an electrically heated fluidized sand bath to control the temperature of the cylinder and its contents. Feed of reactants to the cylinder were from the top of the cylinder to the bottom. The aluminum solids were held in place by a plug of glass wool.

The above results demonstrate that methylchlorodisilanes react with methyl chloride in the presence of aluminum to produce not only more highly methylated disilanes but also a significant proportion of methylchlorosilanes.

EXAMPLE 2

A run was made using materials, apparatus, and procedures, similar to those used in Example 1. In this run, however, tin metal was added as a catalyst for the methylation reaction.

The reactor was charged with 99.5 g of aluminum. The volume of the reactor filled with aluminum was 72.4 cc. Contact zone temperature was 250° C. The DMTCDS feed rate was 11.3 g/hr. MeCl feed rate was 8.8 g/hr. Feeds were continued for a period of 180 minutes. The mole ratio of MeCl/DMTCDS was 3.54/1. At the reactor temperature, the residence time for the feed gases was about 13.2 seconds.

The aluminum used was Alcan 44 aluminum powder. The catalyst was tin metal. The tin was added to the aluminum powder so that the tin content of the solids was about 3925 ppm by weight.

Samples were taken of the total reactor effluent at the end of the run. Table 2 is a summary of the results of the run. The notation of Example 1 is utilized in Table 2.

TABLE 2

| Disilanes | | | | | | | % SiCl Conv | % MeCl Conv | % Me Eff |
|---|---|---|---|---|---|---|---|---|---|
| Me4 | Me3 | Me2 | Me3 | Me4 | Me5 | Me6 | | | |
| 57.3 | 6.3 | 0 | 0 | 0 | 0 | 33.9 | 100 | 80.3 | 100 |

The above results demonstrate that tin is a catalyst that will increase the degree of methylation of both product organsilanes and organodisilanes.

What is claimed is:

1. A process for preparing more highly alkylated silicon compounds having the formula, $$R_a R^i_b SiX_{(4-a-b)}$$ or $$R_f R^i_g Si_2 X_{(6-f-g)}$$

wherein each R is independently selected from a group consisting of methyl and ethyl, and n-propyl; each $R^i$ is independently selected from a group consisting of hydrogen atoms, alkyl, substituted alkyl, alkenyl, aryl, and alkaryl groups; a has a value of 0, 1, 2, 3, or 4, b has a value of 0, 1, 2, 3, or 4, and the sum of a+b is 4 or less; f has a value of 0, 1, 2, 3, 4, 5, or 6, g has a value of 0, 1, 2, 3, 4, 5, or 6, and the sum of f+ g is 6 or less; the sum of a+f is greater than zero and less than 11; and X is an independently selected halogen atom, said process comprising (A) contacting a halodisilane of silicon, having the formula, $$R^i_e X_{6-e} Si_2,$$

or mixture thereof, wherein $R^i$ and X are defined above; and e has a value of 0, 1, 2, 3, 4, or 5, with an alkyl halide, having the formula,

RX, wherein R and X are defined above, in the presence of a metal which serves as a halogen acceptor;
(B) reacting the halodisilane with the alkyl halide in the presence of the metal at a temperature greater than about 150° C. to form the more highly alkylated silicon compound and a halide of the metal; and
(C) isolating and separating the more highly alkylated silane.

2. A process according to claim 1, wherein each R is independently selected from a group consisting of methyl and ethyl.

3. A process according to claim 1, wherein (A) contacting a halodisilane with an alkyl halide in the presence of a metal which serves as a halogen acceptor and (B) reacting the halodisilane with the alkyl halide in the presence of a metal which serves as a halogen acceptor is carried out in the presence of a sufficient quantity of a catalyst effective in improving exchange of said R groups from the alkyl halide with said halogen atoms X of said halodisilane to yield said more highly alkylated silanes.

4. A process according to claim 3, wherein the catalyst is a material that improves contact of the vapors of the reactant alkyl halide and the halodisilane of silicon with the halogen-accepting metal by facilitating increased penetration or disruption of a metal oxide layer on the surface of the metal which serves as a halogen acceptor.

5. A process according to claim 3, wherein the catalyst is a discrete mixture with the halogen-accepting metal.

6. A process according to claim 3, wherein the catalyst is present as an alloy with the halogen-accepting metal.

7. A process according to claim 1, wherein the metal which serves as a halogen acceptor is zinc.

8. A process according to claim 1, wherein the metal which serves as a halogen acceptor is aluminum.

9. A process according to claim 3, wherein the metal which serves as a halogen acceptor is zinc.

10. A process according to claim 3, wherein the metal which serves as a halogen acceptor is aluminum.

11. A process according to claim 10, wherein the catalyst is selected from a group consisting of tin and tin compounds, antimony and antimony compounds, magnesium and magnesium compounds, mercury and mercury compounds, zinc and zinc compounds, aluminum bromide, iron halides, boron, phosphorous, metal phosphorous alloys, metal phosphides, palladium, iodine, hydrogen halides, and mixtures thereof.

12. A process according to claim 9, wherein the catalyst is selected from a group consisting of tin and tin compounds, antimony and antimony compounds, magnesium and magnesium compounds, mercury and mercury compounds, aluminum bromide, iron halides, boron, phosphorous, metal phosphorous alloys, metal phosphides, palladium, iodine, hydrogen halides, copper and copper compounds, and mixtures thereof.

13. A process according to claim 10, wherein the catalyst is selected from a group consisting of tin and tin compounds, antimony and antimony compounds, magnesium and magnesium compounds, zinc and zinc compounds, mercury and mercury compounds, aluminum bromide, iron halides, boron, phosphorous, metal phosphorous alloys, metal phosphides, palladium, iodine, hydrogen halides, copper and copper compounds, and mixtures thereof.

14. A process according to claim 3, wherein the halodisilane has the formula, $$(CH_3)_e Cl_{6-e} Si_2;$$

the alkyl halide is methyl chloride; the halogen acceptor is aluminum; and the catalyst is selected from a group consisting of tin metal and tin compounds, wherein the catalyst is present at a concentration of greater than about 3000 parts per million, based upon the weight of the aluminum; and wherein the halodisilane, the methyl chloride, the aluminum, and the catalyst are contacted at a temperature in a range from about 150° to 250° C.

15. A process for preparing more highly alkylated silicon compounds having the formula, $$R_a R^i_b SiX_{(4-a-b)}$$ or $R_fR^i_gSi_2X_{(6-f-g)}$ wherein each R is independently selected from a group consisting of methyl and ethyl, and n-propyl; each $R^i$ is independently selected from a group consisting of hydrogen atoms, alkyl, substituted alkyl, alkenyl, aryl, and alkaryl groups; a has a value of 1, 2, 3, or 4, b has a value of 0, 1, 2, or 3, and the sum of a+b is 4 or less; f has a value of 1, 2, 3, 4, 5, or 6, g has a value of 0, 1, 2, 3, 4, or 5, and the sum of f+g is 6 or less; and X is an independently selected halogen atom, said process comprising (A) contacting a halodisilane of silicon, having the formula, $R^i_eX_{6-e}Si_2$, or mixture thereof, wherein $R^i$ and X are defined above; and e has a value of 0, 1, 2, 3, 4, or 5, with an alkyl halide, having the formula,

RX, wherein R and X are defined above, in the presence of a metal which serves as a halogen acceptor;

(B) reacting the halodisilane with the alkyl halide in the presence of the metal at a temperature greater than about 150° C. to form the more highly alkylated silicon compound and a halide of the metal; and (C) isolating and separating the more highly alkylated silane.

16. A process according to claim 15, wherein each R is independently selected from a group consisting of methyl and ethyl.

17. A process according to claim 15, wherein (A) contacting a halodisilane with an alkyl halide in the presence of a metal which serves as a halogen acceptor and (B) reacting the halodisilane with the alkyl halide in the presence of a metal which serves as a halogen acceptor is carried out in the presence of a sufficient quantity of a catalyst effective in improving exchange of said R groups from the alkyl halide with said halogen atoms X of said halodisilane to yield said more highly alkylated silanes.

18. A process according to claim 17, wherein the catalyst is a material that improves contact of the vapors of the reactant alkyl halide and the halodisilane of silicon with the halogen-accepting metal by facilitating increased penetration or disruption of a metal oxide layer on the surface of the metal which serves as a halogen acceptor.

19. A process according to claim 17, wherein the catalyst is a discrete mixture with the halogen-accepting metal.

20. A process according to claim 17, wherein the catalyst is present as an alloy with the halogen-accepting metal.

21. A process according to claim 15, wherein the metal which serves as a halogen acceptor is zinc.

22. A process according to claim 15, wherein the metal which serves as a halogen acceptor is aluminum.

23. A process according to claim 17, wherein the metal which serves as a halogen acceptor is zinc.

24. A process according to claim 17, wherein the metal which serves as a halogen acceptor is aluminum.

25. A process according to claim 24, wherein the catalyst is selected from a group consisting of tin and tin compounds, antimony and antimony compounds, magnesium and magnesium compounds, mercury and mercury compounds, zinc and zinc compounds, aluminum bromide, iron halides, boron, phosphorous, metal phosphorous alloys metal phosphides, palladium, iodine, hydrogen halides, and mixtures thereof.

26. A process according to claim 23, wherein the catalyst is selected from a group consisting of tin and tin compounds, antimony and antimony compounds, magnesium and magnesium compounds, mercury and mercury compounds, aluminum bromide, iron halides, boron, phosphorous, metal phosphorous alloys, metal phosphides, palladium, iodine, hydrogen halides, and mixtures thereof.

27. A process according to claim 23, wherein the catalyst is selected from a group consisting of tin and tin compounds, antimony and antimony compounds, magnesium and magnesium compounds, mercury and mercury compounds, aluminum bromide, iron halides, boron, phosphorous, metal phosphorous alloys, metal phosphides, palladium, iodine, hydrogen halides, copper and copper compounds, and mixtures thereof.

28. A process according to claim 24, wherein the catalyst is selected from a group consisting of tin and tin compounds, antimony and antimony compounds, magnesium and magnesium compounds, zinc and zinc compounds, mercury and mercury compounds, aluminum bromide, iron halides, boron, phosphorous, metal phosphorous alloys, metal phosphides, palladium, iodine, hydrogen halides, copper and copper compounds, and mixtures thereof.

29. A process according to claim 17, wherein the halodisilane has the formula, $(CH_3)_eCl_{6-e}Si_2$;

the alkyl halide is methyl chloride; the halogen acceptor is aluminum; and the catalyst is selected from a group consisting of tin metal and tin compounds, wherein the catalyst is present at a concentration of greater than about 3000 parts per million, based upon the weight of the aluminum; and wherein the halodisilane, the methyl chloride, the aluminum, and the catalyst are contacted at a temperature in a range from about 150° to 250° C.

30. A process according to claim 9, wherein the catalyst is selected from a group consisting of tin and tin compounds, antimony and antimony compounds, magnesium and magnesium compounds, mercury and mercury compounds, aluminum bromide, iron halide, boron, phosphorous, metal phosphorous alloys, metal phosphides, palladium, iodine, hydrogen halides, and mixtures thereof.

* * * * *